United States Patent [19]
Cooper et al.

[11] Patent Number: 6,006,387
[45] Date of Patent: Dec. 28, 1999

[54] COLD WATER OZONE DISINFECTION

[75] Inventors: Theodore R. Cooper, Salt Lake City; Allyson T. Toney, West Point; John B. McParlane, Salt Lake City, all of Utah

[73] Assignee: Cyclo3pss Textile Systems, Inc., Salt Lake City, Utah

[21] Appl. No.: 08/565,714

[22] Filed: Nov. 30, 1995

[51] Int. Cl.⁶ .................................................. D06F 39/02
[52] U.S. Cl. ............................ 8/158; 68/13 R; 68/18 R; 68/183; 68/207
[58] Field of Search ................................ 8/158; 68/13 R, 68/18 R, 183, 207; 422/186.12

[56] References Cited

U.S. PATENT DOCUMENTS

| | | | |
|---|---|---|---|
| 1,096,991 | 5/1914 | Blanchard . | |
| 1,823,352 | 9/1931 | Crespi et al. . | |
| 2,189,017 | 2/1940 | Rivat . | |
| 2,529,802 | 11/1950 | Glass | 68/183 |
| 3,065,620 | 11/1962 | Houser | 68/13 R |
| 3,130,570 | 4/1964 | Rentzepis | 68/13 R |
| 3,194,628 | 7/1965 | Cannon | 8/137 |

(List continued on next page.)

FOREIGN PATENT DOCUMENTS

| | | |
|---|---|---|
| 593933 | 9/1925 | France . |
| 6-313194 | 11/1994 | Japan . |
| WO 95/06712 A1 | 3/1995 | WIPO . |

OTHER PUBLICATIONS

Jodlowski et al., "Possibilities of Decolorization of Dye Wastes from the Textile Industry Using the Ozonation Method," *Przeglad Wlokienniczy: 1979*, pp. 37–39, pp. Engl. Tr. 1–13, 1979.

Kurbiel, "Removal of Color, Detergents, and Other Refractory Substances from Textile Wastewater," *EPA–600/2–78–072*, pp. i–xiv, and 248–314, Mar. 1978.

Laundry Logic, Inc., "Laundry Logic Ozone Injection Systems," Bulletin No. OM–105, pp. 1–6, and 16 pages of tables.

Nazarov et al., "Ozonization of Waste (Sewage) in Textile Industry," *Tekstilnaia promushlennost*, pp. 1–13 and 52–56, Jun. 1984.

Rice et al., "Analytical Aspects of Ozone Treatment of Water and Wastewater," Lewis Publishers, Inc., pp. 41–90, 129–159, and 245–255, 1986.

*Primary Examiner*—Philip R. Coe
*Attorney, Agent, or Firm*—Trask, Britt & Rossa

[57] ABSTRACT

The invention includes a method of reducing the microbial population on a textile in a washing machine. The washing machine has an outer shell for containing fluids and an internal assembly for containing textiles. The method includes introducing a wash liquor into the internal assembly, thus contacting the textile with the wash liquor and wetting the textile. The wash liquor is then removed from the internal assembly and the outer shell at a first point. At a second point, a combination of ozone gas, oxygen and/or oxygen enriched air is mixed into the wash liquor being removed from the outer shell to form an ozonated wash liquor. This ozonated wash liquor is re-introduced into the outer shell and internal assembly thus contacting the textile with the ozonated wash liquor for a period of time.

6 Claims, 4 Drawing Sheets

U.S. PATENT DOCUMENTS

| | | | |
|---|---|---|---|
| 3,226,842 | 1/1966 | Morey . | |
| 3,606,996 | 9/1971 | Wolf . | |
| 3,659,096 | 4/1972 | Kompanek . | |
| 3,674,216 | 7/1972 | Blair . | |
| 3,778,229 | 12/1973 | Webster et al. . | |
| 3,780,308 | 12/1973 | Nablo . | |
| 3,836,786 | 9/1974 | Lowther . | |
| 3,875,303 | 4/1975 | Hieber . | |
| 3,877,152 | 4/1975 | Gorman . | |
| 3,891,561 | 6/1975 | Lowther . | |
| 3,899,683 | 8/1975 | Lowther . | |
| 3,903,426 | 9/1975 | Lowther . | |
| 3,904,521 | 9/1975 | Stopka . | |
| 3,916,652 | 11/1975 | Speakman | 68/13 R |
| 3,919,433 | 11/1975 | Senior . | |
| 3,954,586 | 5/1976 | Lowther . | |
| 3,960,673 | 6/1976 | Morrow et al. . | |
| 3,984,697 | 10/1976 | Lowther . | |
| 3,996,474 | 12/1976 | Lowther . | |
| 3,998,714 | 12/1976 | Armstrong . | |
| 4,003,832 | 1/1977 | Henderson et al. . | |
| 4,013,567 | 3/1977 | Emelyanov et al. . | |
| 4,021,347 | 5/1977 | Teller et al. . | |
| 4,035,296 | 7/1977 | Armstrong . | |
| 4,035,301 | 7/1977 | Armstrong . | |
| 4,045,347 | 8/1977 | Armstrong . | |
| 4,053,399 | 10/1977 | Donnelly et al. . | |
| 4,076,617 | 2/1978 | Bybel et al. . | |
| 4,100,073 | 7/1978 | Hopcroft . | |
| 4,101,296 | 7/1978 | Lowther . | |
| 4,139,405 | 2/1979 | Seiberling . | |
| 4,141,686 | 2/1979 | Lewis . | |
| 4,145,007 | 3/1979 | Jetzer . | |
| 4,159,944 | 7/1979 | Erickson et al. . | |
| 4,171,056 | 10/1979 | Hannon et al. . | |
| 4,204,955 | 5/1980 | Armstrong . | |
| 4,214,330 | 7/1980 | Thorsen | 8/149.2 |
| 4,219,415 | 8/1980 | Nassef et al. . | |
| 4,227,653 | 10/1980 | Jetzer . | |
| 4,242,310 | 12/1980 | Greff et al. . | |
| 4,244,712 | 1/1981 | Tongret . | |
| 4,255,663 | 3/1981 | Lewis . | |
| 4,265,747 | 5/1981 | Copa et al. . | |
| 4,283,251 | 8/1981 | Singh | 162/17 |
| 4,300,367 | 11/1981 | Thorsen | 68/5 D |
| 4,304,673 | 12/1981 | Reynolds et al. . | |
| 4,340,489 | 7/1982 | Adams et al. . | |
| 4,343,765 | 8/1982 | Elston et al. . | |
| 4,363,322 | 12/1982 | Andersson . | |
| 4,375,812 | 3/1983 | Vaseen et al. . | |
| 4,379,129 | 4/1983 | Abe . | |
| 4,384,943 | 5/1983 | Stoner et al. . | |
| 4,411,756 | 10/1983 | Bennett et al. . | |
| 4,434,086 | 2/1984 | Hill et al. . | |
| 4,462,880 | 7/1984 | Hill et al. . | |
| 4,476,041 | 10/1984 | Hill et al. . | |
| 4,488,973 | 12/1984 | Hill et al. . | |
| 4,504,446 | 3/1985 | Kunicki et al. . | |
| 4,535,247 | 8/1985 | Kurtz . | |
| 4,578,185 | 3/1986 | Wilson et al. . | |
| 4,595,498 | 6/1986 | Cohen et al. . | |
| 4,617,230 | 10/1986 | Shah et al. . | |
| 4,623,515 | 11/1986 | Frei et al. . | |
| 4,625,432 | 12/1986 | Baltes . | |
| 4,675,023 | 6/1987 | Hyink | 8/447 |
| 4,752,401 | 6/1988 | Bodenstein . | |
| 4,767,405 | 8/1988 | Lokken . | |
| 4,772,411 | 9/1988 | Sprecker et al. . | |
| 4,780,277 | 10/1988 | Tanaka et al. . | |
| 4,804,449 | 2/1989 | Sweeney . | |
| 4,813,210 | 3/1989 | Masuda et al. . | |
| 4,818,488 | 4/1989 | Jacob . | |
| 4,822,563 | 4/1989 | Joslyn . | |
| 4,869,872 | 9/1989 | Baltes . | |
| 4,881,941 | 11/1989 | Dixon | 8/482 |
| 4,912,058 | 3/1990 | Mussi et al. . | |
| 4,915,955 | 4/1990 | Gömöri . | |
| 4,917,586 | 4/1990 | Jacob . | |
| 4,941,270 | 7/1990 | Hoffman . | |
| 4,954,321 | 9/1990 | Jensen . | |
| 4,962,090 | 10/1990 | Sprecker et al. . | |
| 4,963,285 | 10/1990 | Sprecker et al. . | |
| 4,966,717 | 10/1990 | Kern | 210/760 |
| 4,976,920 | 12/1990 | Jacob . | |
| 4,990,494 | 2/1991 | Narula et al. . | |
| 4,995,123 | 2/1991 | Kern . | |
| 5,004,587 | 4/1991 | Tacchi . | |
| 5,008,548 | 4/1991 | Gat . | |
| 5,014,211 | 5/1991 | Turner et al. | 68/17 R X |
| 5,024,766 | 6/1991 | Mahmud . | |
| 5,041,483 | 8/1991 | Burch . | |
| 5,053,140 | 10/1991 | Hurst | 210/704 |
| 5,073,488 | 12/1991 | Matner et al. . | |
| 5,089,098 | 2/1992 | Tacchi . | |
| 5,097,556 | 3/1992 | Engel et al. | 8/158 |
| 5,107,605 | 4/1992 | Yamada et al. | 68/18 R X |
| 5,118,322 | 6/1992 | Wasinger et al. . | |
| 5,123,176 | 6/1992 | Yamada et al. | 68/18 C X |
| 5,154,895 | 10/1992 | Moon . | |
| 5,171,525 | 12/1992 | Jacob . | |
| 5,180,502 | 1/1993 | Nishiki et al. . | |
| 5,181,399 | 1/1993 | Engel et al. . | |
| 5,187,137 | 2/1993 | Terui et al. . | |
| 5,200,158 | 4/1993 | Jacob . | |
| 5,207,237 | 5/1993 | Langford | 134/102.1 |
| 5,211,919 | 5/1993 | Conrad . | |
| 5,223,401 | 6/1993 | Foltz et al. . | |
| 5,236,512 | 8/1993 | Rogers et al. . | |
| 5,244,585 | 9/1993 | Sugimoto . | |
| 5,245,845 | 9/1993 | Langford . | |
| 5,252,484 | 10/1993 | Matner et al. . | |
| 5,258,409 | 11/1993 | Gay . | |
| 5,262,129 | 11/1993 | Terada et al. . | |
| 5,280,876 | 1/1994 | Atkins . | |
| 5,286,447 | 2/1994 | Fannin et al. . | |
| 5,286,700 | 2/1994 | Terui et al. . | |
| 5,302,343 | 4/1994 | Jacob . | |
| 5,306,471 | 4/1994 | Harbert et al. . | |
| 5,322,637 | 6/1994 | O'Grady . | |
| 5,325,600 | 7/1994 | Gentile . | |
| 5,332,511 | 7/1994 | Gay et al. . | |
| 5,348,724 | 9/1994 | Hagimori et al. . | |
| 5,353,745 | 10/1994 | Fahs, II . | |
| 5,360,556 | 11/1994 | Ball et al. . | |
| 5,366,746 | 11/1994 | Mendenhall . | |
| 5,370,793 | 12/1994 | Sugimoto . | |
| 5,373,025 | 12/1994 | Gay . | |
| 5,384,933 | 1/1995 | Wang . | |
| 5,387,350 | 2/1995 | Mason . | |
| 5,393,490 | 2/1995 | Jacob . | |
| 5,409,616 | 4/1995 | Garbutt et al. . | |
| 5,418,167 | 5/1995 | Matner et al. . | |
| 5,422,068 | 6/1995 | Shalaby et al. . | |
| 5,422,185 | 6/1995 | Egami et al. . | |
| 5,423,902 | 6/1995 | Strutz et al. . | |
| 5,424,515 | 6/1995 | Gentile . | |
| 5,433,866 | 7/1995 | Hoppe et al. . | |

| | | | | |
|---|---|---|---|---|
| 5,433,919 | 7/1995 | Baltes . | 5,451,368 | 9/1995 Jacob . |
| 5,433,927 | 7/1995 | Mausgrover et al. . | 5,456,809 | 10/1995 Cooper . |
| 5,443,801 | 8/1995 | Langford . | 5,460,705 | 10/1995 Murphy et al. . |
| 5,444,102 | 8/1995 | Nimitz et al. . | 5,493,743 | 2/1996 Schneider et al. ............... 8/149.2 |

COLD WATER OZONE DISINFECTION

TECHNICAL FIELD

The invention relates generally to a method of reducing the microbial load on textiles. More specifically, this invention relates to a method of disinfecting, sanitizing, or sterilizing textiles involving the use of ozone.

Background

Ozone is an unstable triatomic allotrope of oxygen. It is produced in an energized environment wherein molecular oxygen dissociates into monatomic oxygen which subsequently collides and recombines with an oxygen molecule to form a highly reactive ozone molecule.

Although ozone is primarily employed in disinfection, it can perform other functions such as color reduction, odor and taste removal, algae control, oxidation of inorganic and organic compounds in water and waste-water treatment practices, waste gas treatment and bleaching of paper pulp.

The most prominent features of ozone as a biocide lie in its speed and selectivity in oxidation. Biocidal effects are believed to primarily be achieved through oxidation. Consistent with this belief, the ability of any chemical to reduce microbial viability is in direct proportion to its oxidation potential. Ozone is the fourth most powerful oxidizing agent known; only fluorine, fluorine dioxide, and monatomic oxygen are thought to be more reactive. Ozone possesses an oxidation potential of 2.07 millivolts relative to chlorine gas' 1.36 millivolts. It is important to note that an increased oxidation potential is indicative of an accelerated bacterial kill. The rate of disinfection has been demonstrated to be more than 3,000 times faster than chlorine; thus contact time is a lesser consideration in the application of ozone as a microbicide.

Disinfection with the use of ozone may proceed by oxidation directly and by intermediate hydroperoxy compounds that can interact with cytosolic components. Organic ozone chemistry would predict that oxidized organic compounds containing carbon-carbon double bonds give rise to hydroperoxyalcohols. Evidence exists that organic peroxides exert a stronger bacteriocidal action than hydrogen peroxide due to a greater tendency to decompose. No evidence is believed to exist in the literature of any microorganism that is resistant to the effects of ozone exposure. The application of ozone is preferable due to its compatibility with biota. There are no residual or harmful reaction products downstream particularly in the range of 0–20 ppm. The presence of peroxidic compounds could be perceived to be harmful to the biota, but toxicity studies indicate the contrary to be true. Studies have shown that these compounds are chemically highly unstable and rapidly decompose. It has also been shown that these compounds can be removed by other oxidizing molecules.

This information is in juxtaposition with information generated regarding the toxic effects of chorine and chlorinated products on the general biota as well as on human life. There is some substantiation to the claim that dioxin, a by-product of chlorine, may be linked to cancer and diseases of the human immunological, developmental and reproductive functions.

In addition to demonstrating powerful capabilities in the destruction or inactivation of bacteria, fungi and protozoa; ozone has been shown to be virucidal. The efficacy of ozone has been reported to range from (all of the following values given reported a 99% reduction) 2.2 mg/l for *Escherichia coli* in 19 minutes from raw waste water; 0.02 mg/l for *Candida tropicalis* in 0.30 minutes from ozone-demand free water; 1.2 mg/l for *Naegleria gruberi* in 1.1 minutes from ozone-demand free phosphate buffer solution and 0.2 mg/l for Poliovirus type I in 9 minutes from activated sludge effluent. With regard to bacterial spores (specifically, *Bacillus subtilis* v. *globigii*), ozone has been shown to achieve a four-log reduction within 1.5–2 minutes when water is purged with 3% ozone by weight. Using a non-toxic concentration of 4 µg ozone per ml of serum, ozone can achieve a six-log reduction in the infectious titer of human immunodeficiency virus ("HIV").

Presently, the most commonly employed method of "bioburden" reduction within the washwheel is chlorination. The most actively oxidative form of chlorine, formed by the hydrolysis of chlorine in water, is hypochlorite hypochlorous acid. Studies have shown ozone to be more powerful by factors ranging between 5–1000. Both chemicals limit outgrowth, inactivate or destroy microbes via oxidation but unlike chlorine, ozone's action is more direct, faster and engenders fewer residual considerations. The half-life of ozone in solution is less than 30 minutes and it is highly susceptible to degradation by increased temperature, pH and photolysis by ultraviolet light whereas chlorine generates chlorinated organic compounds which present more of a challenge with regard to removal or neutralization. The application of ozone in disinfection, sanitization or sterilization processes results in improved wastewater quality.

Currently, such as in hospital operating rooms, many garments are disposed of to facilitate containment of blood-borne pathogens as well as other infectious agents. Reuse of these items constitutes an immense saving in capital expenditures; regarding purchase of single-use items and their biohazardous disposal costs, as well as demonstrating environmental responsibility. Reuse of these items generates special consideration for laundry personnel. In this environment, the necessity for a reliable means of reducing the bioburden to acceptable levels is of critical importance.

It would be an improvement in the art to have a relatively economical, reliable method of disinfecting, sanitizing or sterilizing textiles such as garments or healthcare linens.

DISCLOSURE OF THE INVENTION

The invention includes a method of reducing the microbial load on textiles in a washing machine. The washing machine is of the type having an outer shell for containing fluids and an internal assembly for containing textiles. The method includes introducing the textile and a wash liquor into the internal assembly of the washing machine, thus bringing the textile and wash liquor into contact to wet the textile. A combination of ozone gas, oxygen and/or oxygen enriched air is mixed into the wash liquor to form an ozonated wash liquor. This ozonated wash liquor contacts the textile for a period of time ranging from about 3 minutes to 60 minutes.

In one embodiment, the sterilization occurs without significantly altering the color of the textile. This yields a method of reducing the microbial content on a dyed textile to limit viability of an infectious agent believed to be thereon without bleaching or oxidizing the dye. This method comprises contacting the dyed textile with a wash liquor at a temperature of about 50° F. to about 140° F. The wash liquor is an admixture of aqueous solution and surfactant. The textile is thus wetted. A gaseous mixture of ozone gas, oxygen and/or oxygen enriched air is mixed with the wash liquor to form an ozonated wash liquor containing from about 0.01 ppm to about 50 ppm ozone. The ozonated wash liquor is then allowed to contact the textile for a period of time ranging from about 3 minutes to about 60 minutes (preferably 5 to 15 minutes) thus limiting viability of any said infectious agent on said textile, but not unduly altering or removing the dye in the textile.

The process results in disinfected, sanitized, deodorized and/or sterilized textiles. As shown herein, bacterial spores are killed. Due to ozone's higher oxidation potential; the duration of the wash cycle can be reduced relative to those cycles using chlorine as a biocide while attaining the same or higher biocidal capabilities. Wash temperatures and alkalinity can also be reduced. These contribute to increased textile life by decreasing stress on the fabric through limited mechanical action, more neutral pH's and lower temperatures. It also enhances washroom throughput.

BEST MODE OF THE INVENTION

Although not per se forming part of the instant invention, as depicted in FIGS. 1–5, a washing machine useful to practice of the herein described methods is preferably guided by a system of operation that uses electro-mechanical devices that are directed by electro-mechanical controls, under program control, via a microprocessor in order to deliver the correct concentrations and volume amounts of ozone gas, as well as control and monitoring of pH, temperature and time of various cycles.

In FIGS. 1–5, the reference numeral 1 generally designates a laundry ozone injection system. The system 1 generally includes an ozone generator unit 2 and an ozone distribution panel 3 which cooperate to distribute ozone to a plurality of washing machines 4 to enhance the laundry process thereof. The distribution panel 3 includes an ozone distribution controller or main controller 5 which detects the washer cycles of the washers 4 and enables the delivery of ozone to the washers 4 only during selected washer cycles by controlling the state of ozone control valves 6.

Figures 1, 2:
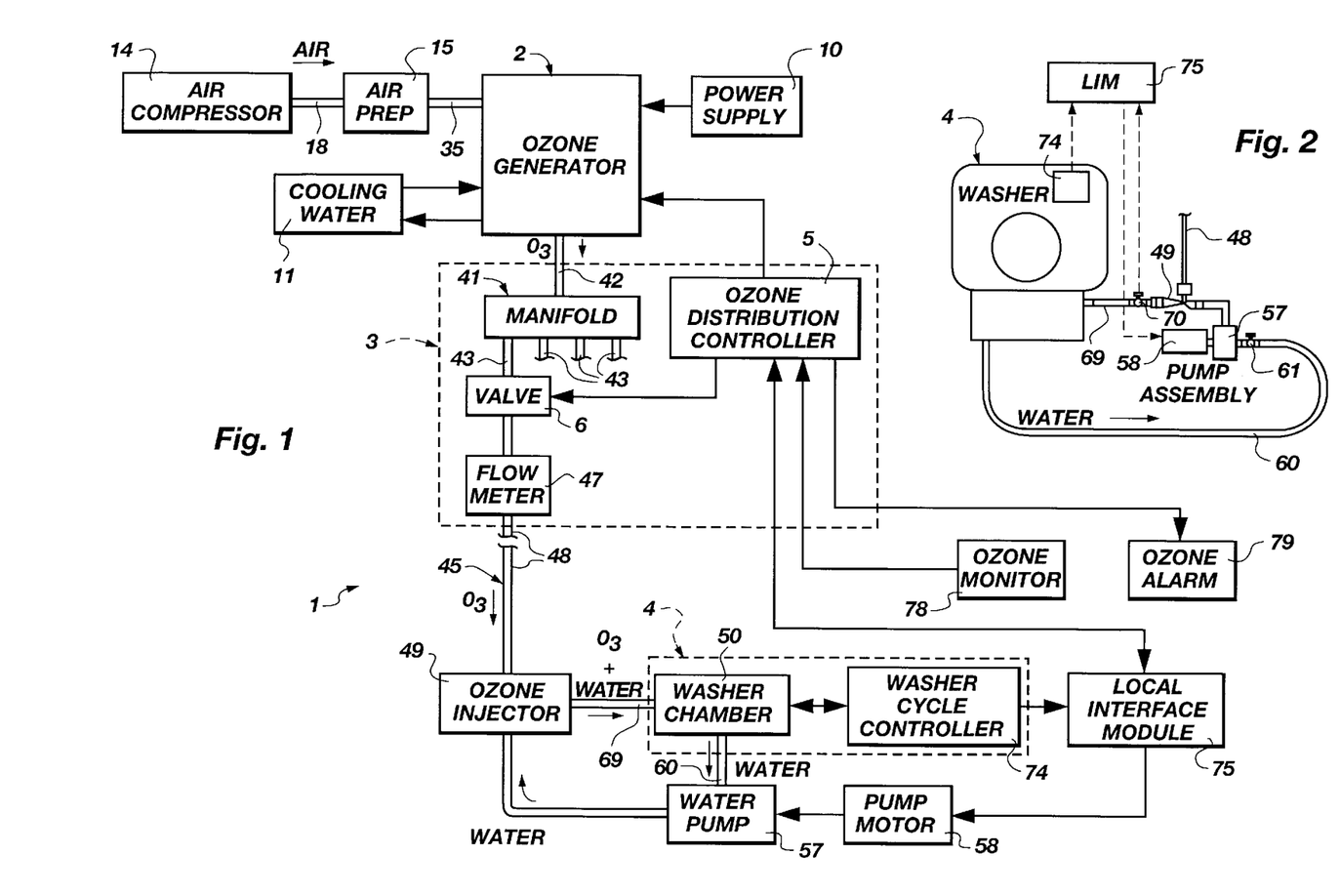
FIG. 1 is a block diagram illustrating the principal components of laundry ozone injection system useful for practicing the present invention.
FIG. 2 is a diagrammatic view of a washing machine station which receives ozone from the ozone injection system useful for practicing the present invention.
Figure 3:
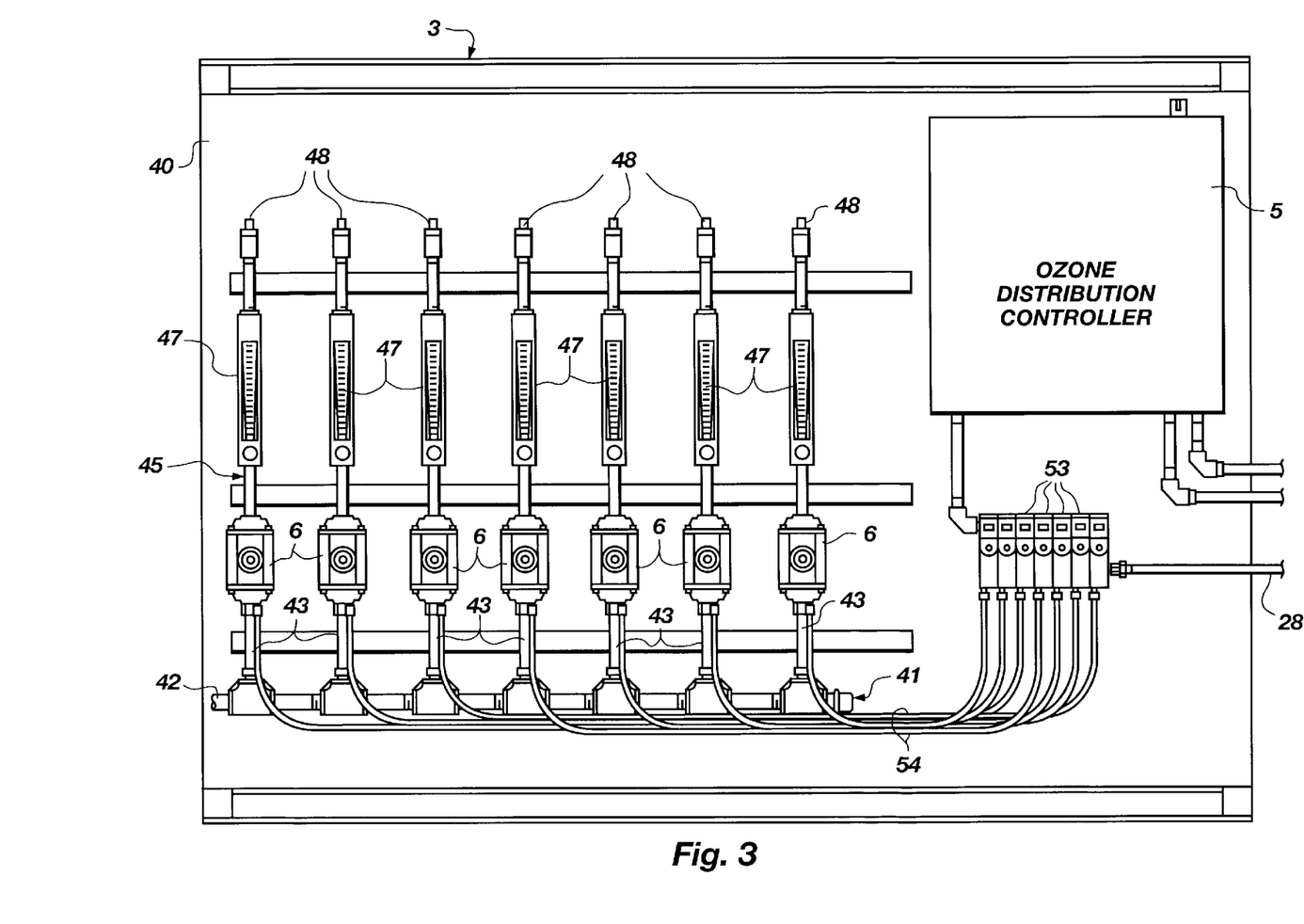
FIG. 3 is a front elevational view of a main panel of an ozone injection system.

The ozone generator 2 may be one of a number of devices for generating ozone from air, oxygen or air enriched with oxygen, and its required capacity depends on the number and size of the washers 4 installed in the washroom of the laundry facility and the types of laundry loads processed therein. An exemplary ozone generator 2 is the model G-28 manufactured by PCI Ozone and Control Systems, Inc. of West Caldwell, N.J. In general, the illustrated ozone generator 2 generates ozone by passing dry air or oxygen through a corona discharge produced by a high voltage at a high frequency which is applied to coaxial electrodes (not shown) within the generator 2. The electrode voltage is derived from three phase 460 volt power by an associated power supply 10, which has a current capacity of 30 amperes. The temperature of the generator 2 is controlled by cycling cooling water 11 through the electrodes. In a preferred mode, the ozone gas is generated from oxygen or oxygen-enriched air by a corona discharge device that produces concentrations ranging between about 1% to about 15% by weight of ozone.

The ozone output of the generator 2 can be controlled by the main controller 5 by an analog signal level therefrom. In general, the ozone output is controlled by controlling the frequency of the ozone generating power applied to the electrodes of the generator 2. The ozone output of the generator 2 may also be varied by controlling the voltage level of the applied power. The illustrated ozone generator 2 may be controlled to vary its ozone output from about ten per cent to full rated output. The main controller 5 also has the capability of completely disabling the generator 2 to entirely shut down the generation of ozone.

Figure 5:
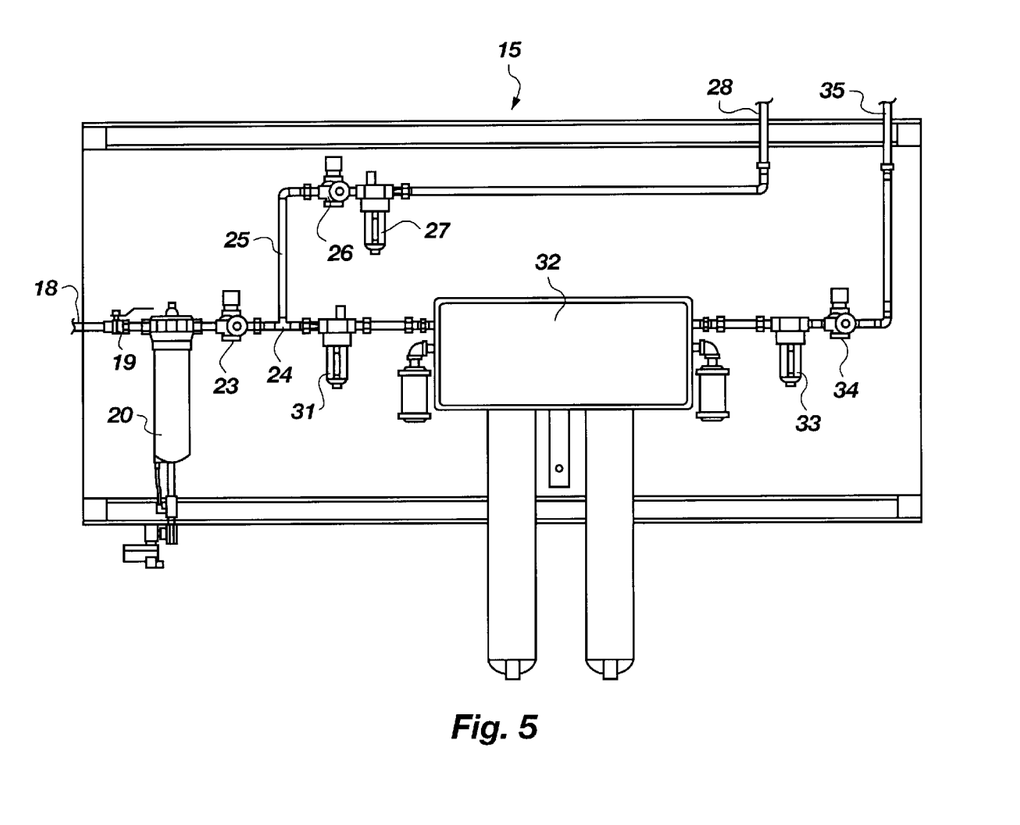
FIG. 5 is an elevational view of an air preparation unit of the ozone injection system useful in the practice of the present invention.
Figure 6:
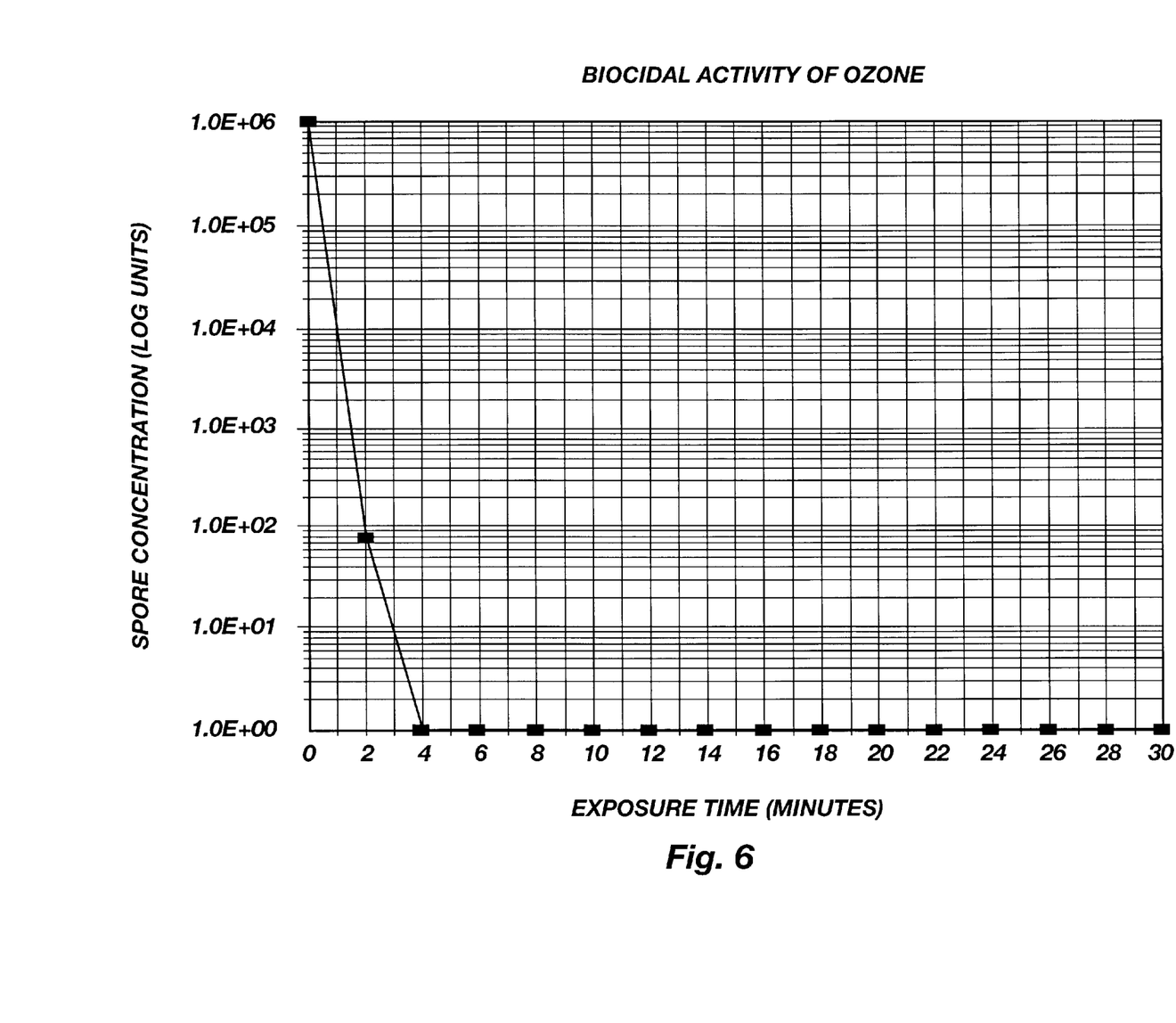
FIG. 6 is a graph depicting the results of EXAMPLE III (spore concentration (log) vs. time in minutes).

In the present invention, the ozone generator receives compressed air from an air compressor 14 through an air preparation unit 15 which filters and dries the air and regulates the pressure thereof. Referring to FIG. 5, the air preparation unit 15 receives compressed air from the compressor 14 at a flow rate of about 25 SCFM (standard cubic feet per minute) and at a pressure of 80–100 psi (pounds per square inch). A supply conduit 18 from the compressor 14 connects to a multiple stage pre-filter 19 through a manually operated ball valve 20. A first pressure regulator 23 regulates air pressure to a T-connector 24 at 80 psi. A branch conduit 25 from the connector 23 leads to a second 80 psi regulator 26, a lubricator 27, and an auxiliary conduit 28 which connects to the main panel 3 for a purpose which will be detailed below. The T-connector 24 also connects to a coalescing filter 31 and a twin regenerative air dryer 32 which removes moisture from the compressed air fed to the ozone generator 2. From the air dryer 32, the air passes through a general purpose filter 33 and a third regulator 34 to provide air at 15 psi to a main air supply conduit 35 which supplies air to the ozone generator 2.

The ozone distribution or main panel 3 (FIG. 3) includes a panel wall 40 supporting an ozone distribution manifold 41 which receives ozonated compressed air from a main ozone supply conduit 42 and makes it available to a plurality of manifold outlet conduits 43. Each outlet conduit 43 forms an ozone distribution circuit 45 between the panel 3 and a washer 4, one circuit 45 being illustrated diagrammatically in FIG. 1. It should be understood that the system 1 has the capability of accommodating a number of such circuits 45, depending on the ozone capacity of the ozone generator 2, the ozone requirements of the particular washers 4, and the ozone requirements for the types of laundry loads which the washers 4 are intended to clean.

Each ozone distribution circuit 45 includes one of the ozone valves 6, a flow meter 47, an ozone feed conduit 48, and an ozone injector 49 which fluidically connects to the washer chamber 50 of a washing machine 4. The illustrated ozone valves 6 are compressed air actuated ball valves, which have been determined to be the most appropriate type of valve for use as the valves 6 in the system 1. Other types of valves could, alternatively, be employed as the valves 6. Each valve 6 is operated by the main controller 5 through a respective solenoid operated valve 53. The ozone valves 6 and the solenoid valves 53 are normally closed. The solenoid valves 53 receive compressed air from the air preparation unit 15 by way of the auxiliary air conduit 28 and are interfaced to the main controller 45 whereby the valves 53 are individually opened to feed compressed air to the ozone valves 6 to open same to thereby feed ozone into the respective ozone feed conduits 48. The flow meters 47 may be conventional "rotameter" type flow meters and are calibrated to indicate a flow range of 1–10 SCFM. The illustrated flow meters 47 incorporate adjustable needle valves (not shown) to vary the flow rate therethrough according to the load capacity of the associated washers 4.

Figure 4:
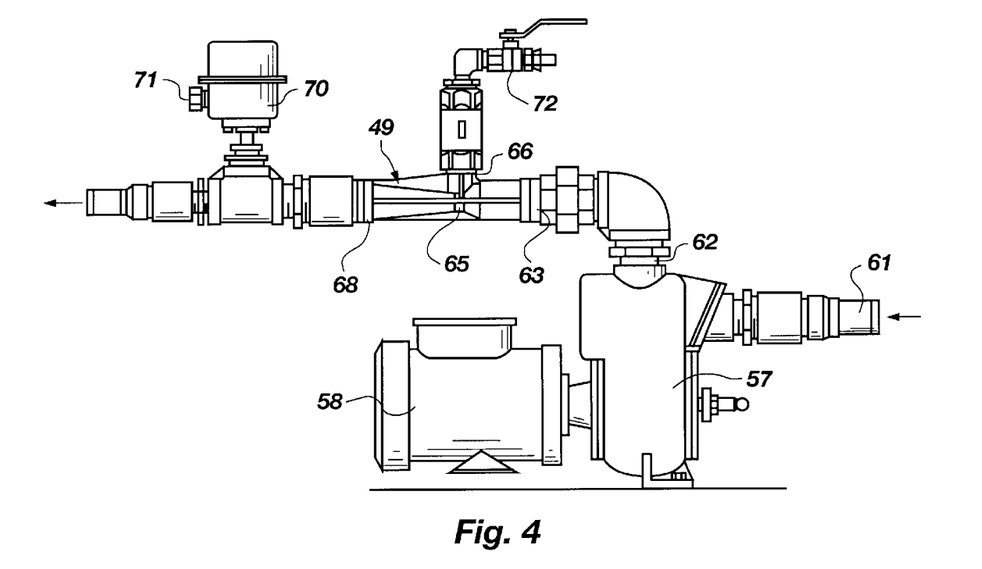
FIG. 4 is an enlarged side elevational view of an ozone injector assembly of an ozone injection system.

Referring to FIG. 1, each washing machine 4 has a water pump 57 which cycles water from the washer chamber 50 through the ozone injector 49 in which ozone is entrained in the water and back to the washer chamber 50. The pump 57 is a centrifugal pump and is driven by a pump motor 58 under control of the main controller 5. Referring to FIG. 4, the pump 57 receives water from a drain conduit or hose 60 through a pump intake connector 61. A pump outlet 62 is connected to a water feed connector 63 of the ozone injector 49. The ozone injector 49 is a venturi type of device in which a throat region 65 of reduced cross sectional area causes a drop in the pressure of fluid passing therethrough. An ozone feed connector 66 fluidically communicates with the throat region 65 and feeds ozonated compressed air thereinto.

As a result of the pressure differentials between the ozonated air and the water, the ozonated air is entrained in the water "explosively" as microbubbles, which increases the oxidizing effectiveness of the ozone in the washer chamber 50 over larger bubbles due to a relatively higher surface area per unit volume of the smaller bubbles. The smaller bubbles can, thus, dissolve a higher percentage of ozonated air in the water than larger bubbles for reaction with the soils and stains in the wash load. In one preferred mode, the combination of ozone gas, oxygen and/or oxygen enriched air introduced into the wash liquor comprises bubbles of gas having a size from about 5 microns to about 5000 microns in diameter entrained in the liquid portion of the wash liquor.

The ozone injector 49 has an injector outlet 68 which is connected to a return conduit or hose 69 and which carries the water with ozonated air therein back to the washer chamber 50. A pressure switch 70 is mounted in the return line 69 and includes a cable connector 71 which is interfaced to the main controller 5 to signal that water under pressure is present in the return line 69. A manually operable ball valve 72 is positioned in the ozone feed conduit 48 and provides a means of positively cutting off the flow of ozone to the ozone injector 49, as for repair and maintenance of the washers 4 or if ozone leaks are detected.

The washers 4 are conventional industrial washing machines which are operated through various washer cycles under control of a washer cycle controller 74. Each washer 4 has a local interface module (LIM) 75 which is interfaced to the washer cycle controller 74, the pump motor 58, the pressure switch 70, and the ozone distribution controller 5 The module 75 provides a means of communication between the main controller 5 and the washer 4 by which the main controller 5 detects the current washer cycle and controls operation of the ozone valve 6 and the pump motor 58. The washer cycle controllers 74 in current operation range from electromechanical controllers in older models to digital and microprocessor controllers in more modern washers 4. Thus, the local interface modules 75 must be configured according to the general type of washer controller 74 employed and also to differences between the controllers 74 of various manufacturers thereof.

A local interface module 75 can detect the current washer cycle from washer cycle controllers 74 by detecting patterns of switch and relay states or patterns of logic states within the washer cycle controller 74. The interface module 75 can be made "intelligent" whereby the particular module 75 is programmed to interpret the patterns of switch, relay, or logic states, and merely communicates an enable or inhibit signal to the main controller 5. Alternatively, the interface module 75 may communicate more detailed data representing the logic patterns to the main controller 5 which then determines the current washer cycle. The ozone distribution or main controller 5 is preferably a programmable logic controller but may also be implemented as a personal type computer with appropriate interfacing and programming, or the like. The main controller 5 may be programmed to vary the ozone output of the ozone generator 2 according to the number and load capacity of washers 4 which are active at a given time.

In general, it is desirable to inject ozone into a washer chamber 50 whenever significant quantities of water (or "wash liquor") are present, as during soak, wash, and rinse cycles. Additionally, it might be desirable to inject ozone into the washer chamber 50 during portions of fill and drain cycles. During such cycles, water is continuously recycled through the washer chamber 50 by the pump 57, and ozone is injected into the recycled water by the ozone injector 49.

When a washer cycle in which ozone is to be injected is detected, the main controller 5 first activates the pump motor 58 and opens the associated solenoid valve 53 to cause opening of the associated ozone valve 6 whereby ozone is communicated from the manifold 41 to the ozone injector 49. At the end of a motor delay period to allow the pump 57 to reach a steady state flow rate, the controller 5 determines the state of the pressure switch 70 to determine that water is actually present in the ozone injector 49. If not, the controller 5 closes the valves 6 and activates an alarm. When the interface module 75 detects a washer cycle in which the injection of ozone is not desired, the flow of ozone from the manifold 41 is terminated by disabling the pump 57 and closing the valves 53 and 6.

Preferably, one or more ozone monitors 78 are positioned about the washroom having the washers 4 installed therein to detect excessive levels of ambient ozone in the washroom. The ozone monitors 78 are interfaced to the main controller 5 which may also have an ozone alarm 79 interfaced thereto. Upon detecting an excessive level of ambient ozone by the monitors 78, the main controller 5 disables the ozone injection process for all the washers 4 in washroom by disabling the ozone generator 2, and sounds the alarm 79 to alert workers.

Virtually all of the ozone injected into the washer chambers 50 is consumed. Thus, the detection of excessive levels of ambient ozone usually implies a leak in the plumbing between the distribution panel 3 and the washers 4. The number and placement of ozone monitors 78 in a laundry washroom is generally determined by the size and airflow patterns therein.

The ozonated wash liquor is preferably re-introduced into the outer shell under a positive pressure force that is developed by a device (e.g. a pump) that causes a pressure differential between the first point in which the wash liquor has been removed from the outer shell and the second point at which the ozone, oxygen and/or oxygen enriched air are dissolved into the wash liquor.

A wash liquor is an aqueous solution. Preferably, the water used in the wash liquor is "softened water". Preferably the wash liquor also contains compounds such as surfactants (nonionic, anionic or cationic), detergents, soaps or mixtures thereof.

In this mode, the concentration of ozone in the ozonated wash liquor ranges from about 0.01 ppm to about 50 ppm (more preferably 5 to 30 ppm $O_3$) depending upon the nature of the textile, the soil type and content, and the desired level of microbial reduction.

A "significant" decrease in color intensity is dependent upon the fabric to be treated, its color and its use, but will generally be an amount of "bleaching" imperceptible to the human eye. Alternatively, a decrease in original color intensity can be measured with a spectrophotometer using standard techniques such as those developed by the American Association of Textile Chemists and Colorists ("AATCC").

The pH of the ozonated wash liquor is monitored, and the pH of the ozonated wash liquor is maintained at a pH from about 4 to about 10.

The temperature of the wash liquor may also be monitored by, for example a thermostat, and is preferably maintained at a temperature in the range of about 50° F. to about 140° F., more preferably from 60 to 110° F.

The invention is further explained by the following illustrative EXAMPLES:

EXAMPLE I

1. PURPOSE: A protocol was developed to determine the resistance of various organisms to sterilization utilizing ozone gas. Six organisms were identified as being useful in determining the efficacy of ozone gas as a biocide. The data generated was used to determine the most resistant organism to ozone exposure. The six organisms listed here are commonly available and can be tested without significant precautions for the protection of personnel from pathogenic microorganisms.

The intent was to expose these six organisms to the level of ozone used in a medical sterilization device and thereby decipher which is the most resistant organism as demonstrated by its ability to maintain viability. The organism which endures ozone exposure the longest without becoming sterilized (sterility is defined as completely dead, rendered unable to grow in an optimal growth medium for that organism) was considered the most resistant. Upon this determination, the qualification, validation and operational testing of a medical equipment sterilization device can proceed utilizing only this most resistant organism.

The microorganisms tested were as follows: *Bacillus subtilis* v. *niger* (ATCC 9372 or 19659), *Bacillus stearothermophilus* (ATCC 7953), *Clostridium sporogenes* (ATCC 3584), *Staphylococcus aureus* (ATCC 6538), *Salmonella choleraesuis* (ATCC 10708), and *Pseudomonas aeruginosa* (ATCC 15442). The ideal cell density used was $10^6$, with a minimum of $10^4$ and a maximum of $10^7$. Using a minimum number of three runs the most resistant organism was determined to be *Bacillus stearothermophilus*.

EXAMPLE II

1. PURPOSE: Due to the lack of pathogenicity, ease in detection due to its obligate thermophilic growth, its accessibility and the information obtained from EXAMPLE I; *Bacillus stearothermophilus* was chosen as an initial ozone wash test organism.

Initial testing was performed using suspensions of *B. stearothermophilus* in sterile, distilled water at a cellular density of $2\times10^4$ spores/ml. Ozone was introduced to the solution through a sparger connected to a corona discharge generator. Bubble size ranged from about 50 microns to about 5000 microns in diameter. The ozone concentration ranged from about 4 ppm to about 20 ppm at an approximate temperature of 18° C. The test was carried out for thirty minutes with samples drawn at one minute intervals up to ten minutes and every five minutes thereafter. The data from this initial experiment indicated that the spores were not viable after a three minute exposure to ozone under these conditions

EXAMPLE III

Subsequent testing was performed in a washwheel containing a wash liquor composed of several constituents. Greater than five-log microbial reduction was demonstrated using ozone concentrations of approximately 1 ppm to 5 ppm at temperatures ranging from about 50° F. up to about 140° F. The diameter of the bubbles generated ranged from about 5 microns to 3000 microns in a wash liquor pH ranging from about 4 to 10 at various stages of the formula.

EXAMPLE IV

Decreases in color intensity in dyed textiles swatches are measured with a LABSCAN II spectrophotometer available from Hunterlab of Reston, Va. using the AATCC "grayscale" standards (use of a series of 5 color plates and compare the color plates to swatch samples). Using the process of EXAMPLE II and EXAMPLE III various dyed textiles are not bleached significantly, and the color changes are not perceptible to the human eye.

References herein to specific Examples or embodiments should not be interpreted as limitations to the invention's scope which is determined by the claims.

What is claimed is:

1. A method of reducing the microbial content on a dyed textile to inactivate or limit the growth potential believed to be thereon without significantly altering or removing the dye, said method comprising:

contacting the dyed textile with a wash liquor at a temperature of about 50° F. to about 140° F., said wash liquor comprising an admixture of aqueous solution and surfactant, thus wetting the textile;

combining a gaseous mixture of ozone gas, air and/or oxygen and/or oxygen enriched air with the wash liquor to form an ozonated wash liquor containing from about 0.01 ppm to about 50 ppm ozone;

and re-contacting said ozonated wash liquor with the dyed textile for a period of time of about 3 minutes to about 60 minutes thus inactivating any microbes present on said dyed textile without decreasing the dyed textile's color intensity significantly.

2. A method of sterilizing a dyed textile to kill an infectious agent believed to be thereon without significantly bleaching the dye, said method comprising:

contacting the dyed textile with a wash liquor at a temperature of about 50° F. to about 140° F., said wash liquor comprising an admixture of aqueous solution and surfactant, thus wetting the dyed textile; removing wash liquor from the dyed textile; combining a gaseous mixture of oxygen and ozone gas with the removed wash liquor to form an ozonated wash liquor containing from about 0.01 ppm to about 50 ppm ozone; and re-contacting said ozonated wash liquor with the dyed textile for a period of time of about three to about sixty minutes thus killing any of said infectious agent on the dyed textile.

3. The method of claim 2 wherein said infectious agent is selected from the group consisting of *Salmonella choleraesuis, Staphylococcus aureus, Pseudomonas aeruginosa, Clostridium sporogenes, Bacillus subtilis, Bacillus stearothermophilus*, and mixtures thereof.

4. The method according to claim 2 wherein the wash liquor's temperature is maintained between about 60° to 110° F.

5. The method according to claim 2 wherein the ozonated wash liquor contains from about 5 ppm to about 30 ppm ozone.

6. The method according to claim 2 wherein said ozonated wash liquor is re-contacted with the dyed textile for a period of time of about five to about thirty minutes.

* * * * *